United States Patent [19]

Solman et al.

[11] Patent Number: 5,208,615

[45] Date of Patent: May 4, 1993

[54] OPTICAL ARRANGEMENTS FOR READING DEFICIENCIES

[75] Inventors: Robert T. Solman, Bronte; Stephen J. Dain, Brighton Le Sands, both of Australia

[73] Assignee: Unisearch Limited, Kensington, Australia

[21] Appl. No.: 603,125

[22] Filed: Oct. 25, 1990

[30] Foreign Application Priority Data

Oct. 27, 1989 [AU] Australia .................................. PJ7119

[51] Int. Cl.$^5$ .............................................. G02C 7/10
[52] U.S. Cl. ......................................... 351/44; 351/45; 351/49
[58] Field of Search ................. 351/44, 45, 47, 159, 351/202, 203, 49

[56] References Cited

U.S. PATENT DOCUMENTS

| | | | |
|---|---|---|---|
| 4,698,022 | 10/1987 | Gilson | 351/47 |
| 4,943,152 | 7/1990 | Whelen | 351/49 |

Primary Examiner—Bruce Y. Arnold
Assistant Examiner—Hung Xuan Dang
Attorney, Agent, or Firm—Ladas & Parry

[57] ABSTRACT

A method of reducing the impact of a reading deficiency caused by a slow transient response comprises the steps of inserting a light diffuser in a reader's light path to attenuate the high spatial frequency information mediated by the cone receptors of the eye(s) of the reader, and inserting a chromatic filter which limits stimulation to the red and/or green cone receptors relative to stimulation of the blue cone receptors in the eye(s) of the reader whereby the magnitude of the cone mediated sustained response of the reader is reduced towards a more normal balance relative to the impaired transient response of the reader. An apparatus for reducing the impact of a reading deficiency caused by a too slow transient response of a reader comprises a light diffuser and a chromatic filter to limit the red and/or green mediated sustained transmission relative to the blue cone mediated transient transmission, the diffuser and filter being locatable in the reader's light path. Also disclosed is a method of testing a patient for impaired transient response, a test kit for testing for impaired transient response, and an optical prescription lens prescribed in accordance with the above method of testing.

13 Claims, 1 Drawing Sheet

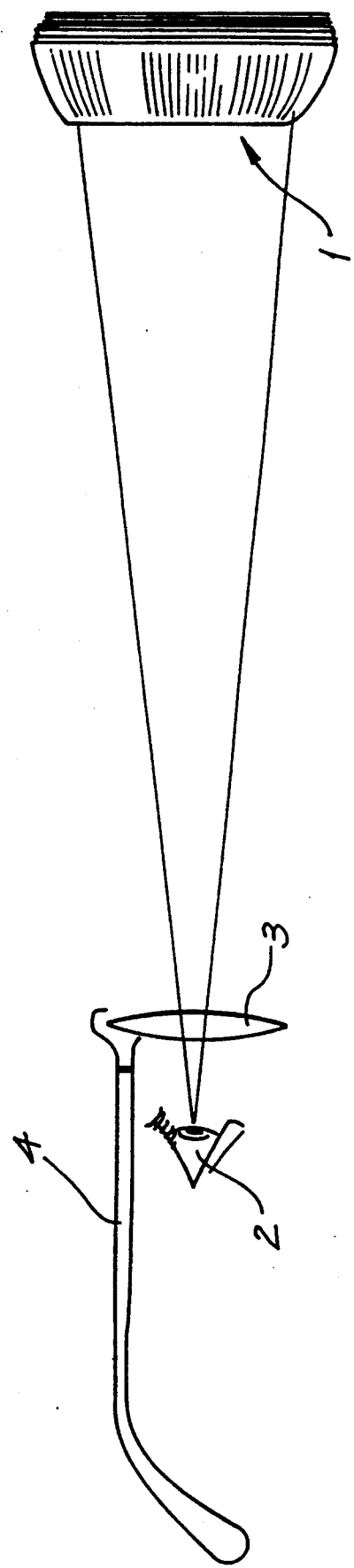

OPTICAL ARRANGEMENTS FOR READING DEFICIENCIES

The present invention relates to reading disabilities and, in particular, to a disability caused by a visual disorder in the channels processing global or low spatial frequency information, termed a transient deficit. The present invention provides a method of, and apparatus for, reducing the impact of the transient deficit on reading, together with a method of testing a patient for this deficiency, a test kit used for carrying out the testing and the resulting prescribed optical lens(es).

BACKGROUND ART

Patients who suffer from disabilities which are specific to reading are generally less sensitive when measured for pattern contrast sensitivity at low spacial frequencies and they generally have greater difficulty in detecting visual flicker than normal readers. In addition, they exhibit slower rates of visual search and have greater difficulty than normal readers in perceptual grouping tasks. Also they require longer separation times before they can correctly report which of two temporally asynchronous patterns appeared first, and they make larger errors when asked to specify the spatial location of a flashed pattern. However, there is no obvious visual problem to account for this disability in that if the patient's eyes were tested by an optometrist they would be found to be essentially normal.

It is known from a published paper (Williams M. C., Brannan J. R. and Latrigue E. K. "Visual Search in Good and Poor Readers" Clinical Vision Sciences 1 Pages 367-371 (1987) that improved visual search results can be achieved if a certain degree of blur is provided by the use of especially prepared diffusing filters which have the effect of removing some of the medium to high spatial frequency information perceived by the viewer.

It is also known to use tinted glasses termed "Irlen Lenses" for the treatment of reading problems, however, there is no rigorous or systematic way in which the colour of the tint which produces either an improved, or optimum, result can be determined. Rather, various subjective judgements as to the efficacy of various tints are made on the basis of the patient's reported perceptions.

As a consequence of the subjective nature of the Irlen Lenses procedures, the procedures are extremely time consuming and do not provide a sound basis for prescription. It is also extremely difficult to determine whether or not the patient is improving as a result of the particular tinted lenses selected.

The present inventors have discovered arrangements which are based upon the sustained and transient theory of visual perception and which enable a predictive basis for improved results to be achieved, thereby enabling not only greater overall improvement, but also a substantial reduction in the time required for testing prior to the prescription of corrective apparatus, and indeed the ability to be able to prescribe at all.

SUMMARY OF THE INVENTION

In accordance with one aspect of the present invention there is disclosed a method of reducing the impact of a reading deficiency caused by a slow transient response of a reader, said method comprising the steps of inserting a light diffusion means in the reader's light path to attenuate the high spatial frequency information mediated by the cone receptors of the eye(s) of the reader, and inserting a chromatic filter which limits stimulation to the red and/or green cone receptors relative to stimulation of the blue cone receptors in the eye(s) of the reader whereby the magnitude of the cone mediated sustained response of the reader is reduced towards a more normal balance relative to the impaired transient response of the reader.

In accordance with a second aspect of the present invention there is disclosed apparatus for reducing the impact of a reading deficiency caused by a too slow transient response of a reader, said apparatus comprising light diffusion means and chromatic filter means to limit the red and/or green mediated sustained transmission relative to the blue cone mediated transient transmission, said diffusion means and filter means being locatable in the reader's light path. Preferably the diffusion means and filter means are combined within a spectacle lens.

In accordance with a third aspect of the present invention there is disclosed a method of testing a patient for impaired transient response, said method comprising the steps of 1) selecting one combination diffusion and chromatic filter from a set of such filters each of which removes an amount of high spatial frequency information above a corresponding predetermined number of cycles per degree, varies the relative levels of stimulation to the red and/or green cones versus the blue cones, and varies the total amount of light transmitted,
2) having the patient carry out a perceptive task sensitive to the transient response whilst viewing the task objects through said selected combination filter,
3) carrying out steps (1) and (2) as necessary to determine an optimum combination filter, and
4) having the patient carry out a reading or reading related task whilst viewing the task objects through the optimum combination filter.

In accordance with a fourth aspect of the present invention there is disclosed a test kit for testing for impaired transient response, said kit comprising in combination.

a set of combination diffusion and chromatic filters each of which removes an amount of high spatial frequency information above a corresponding predetermined number of cycle per degree, varies the relative levels of stimulation to the red and/or green cones versus the blue cones, and varies the total amount of light transmitted;

transient response sensitive perceptive task objects, reading or reading related task objects, and
means to enable objects to be viewed through the combination of a diffuser and a chromatic filter.

In accordance with a fifth aspect of the present invention there is disclosed an optical prescription lens prescribed in accordance with the above described method of testing and comprising said selected optimum combination filter.

BRIEF DESCRIPTION OF THE DRAWING

The sole figure is a schematic side elevation showing a patient viewing an object with the combination diffusion and chromatic filter combined within a spectacle lens.

DETAILED DESCRIPTION

An embodiment of the present invention will now be described with reference to the drawing.

The sustained and transient theory of visual perception is based upon two mutually inhibitory physical processes. The transient response is thought to be mainly initiated by receptors which are located all over the retina, with big receptive fields and having a very fast rate of information transfer. They are thought to be particularly responsive in the range of spatial frequencies from about 0.5 to about 2 cycles per degree.

The sustained response is thought to be mediated or initiated by the cone receptors which are concentrated in the foveal region of the retina and which have small receptive fields and having a relatively slow information transfer rate. They are particularly responsive to spatial information in the range of from 4 to 32 cycles per degree.

Spatial frequency information may be best understood by considering a pattern formed from alternate light and dark columns which therefore has an overall striped appearance. If the columns are each broad and relatively widely spaced, then what is perceived by the eye is low spatial frequency information. However, as the width of the columns decreases and the number of columns in a given area of pattern increases, so the spatial frequency information passes from medium to high spatial frequency information.

It is thought that the sustained response is what gives rise to acuity and enables the fine detail of an object to be perceived. The sustained response transmits information relatively slowly but does so for the duration of an eye fixation. On the other hand, the transient response transmits information relatively quickly but only operates for brief periods at the begining, and at the end, of the eye fixation. The two processes are mutually inhibitory and it is thought that transient-on-sustained inhibition is of particular importance in reading. This is because the onset of transient activity terminates the continuing response of the previous sustained activity. As a consequence, this onset of transient activity separates the information encoded during a sequence of different eye fixations. If the information from different fixations was not separated during its transmission, the overlap of words and letters would create confusion during the stages of recognition and interpretation.

Research in the last ten years shows that low spatial frequency, or the transient processing, component of visual encoding is weak for approximately 70% of specific reading disability cases. In addition, it would appear that there is no specific way of boosting or improving the transient response of such readers.

Rather than attempt to boost the transient response of such readers in some way, the present inventors propose that the sustained response of the reader be attenuated so that a more normal balance between the transient response and the sustained response is achieved. Furthermore, it is proposed that the sustained response be attenuated in two ways.

Firstly, by the provision of "blur" in the form of the diffusion property of the filter to remove some of the medium to high spatial frequency information since a high level of acuity is thought not to be necessary for reading and this information tends to "over power" the low level of transient response.

In addition, in order to further inhibit the sustained response, the chromatic property of the filter is provided in combination with the diffusion property in order to decrease the relative strength of the responses from the red and/or the green cones compared to the strength of the responses from the blue cones. Since the cone receptors which mediate or initiate the sustained response essentially respond to red and/or green light, this can be done by providing a chromatic filter which inhibits the transmission of these wavelengths.

The drawing illustrates the situation schematically in that an object 1 such as the page of a book is being viewed by the eye 2 of the patient via a lens 3 combining diffusion with chromatic filtering. For convenience the lens 3 is held in a substantially conventional spectacles frame 4.

Since the optimal spatial frequency for reading is approximately 10 cycles per degree, the diffusion property preferably substantially attenuates all spatial frequency information having a frequency higher than approximately 10 cycles per degree. In addition, the chromatic property is required to limit the input to the red and green cones (blues). Thus the chromatic filter typically appears blueish in colour.

The combined diffusion with chromatic filtering lens may be realised in any one of a number of ways. For example, the diffuser can be realised by means of two spaced planes of glass or crystals, by the use of a wrinkle surface, or a defraction grating. The lens itself may be either glass or plastic and can, if desired, utilize gradient index lenses.

In order to carry out a transient deficient test for the purposes of prescription, a test kit is provided for use by a qualified optometrist who, prior to conduct of the test kit is provided for use by a qualified optometrist who, prior to conduct of the test will have undergone a short training course. The kit consists of a set of diffusers combined with chromatic selection filters. Total visible transmittance of these filters will vary between about 15% and 75%, and removal of high spatial frequency information will vary between about 12 cycles per degree and 25 cycles per degree. With preferable transmittance values of 15%, 30%, 45%, 60% and 75%, and high spatial removal above 12 cycles per degree, 14.4 cycles per degree, 17.3 cycles per degree, 20.7 cycles per degree and 24.9 cycles per degree (all at 100% contrast), the kit preferred contains twenty five of these filters.

In addition, the kit includes a plurality of perceptual task objects for performing tasks sensitive to deficient transient processing or weak transient-on-sustained inhibition. Such tasks are known per se and the task can be selected from the group of tasks consisting of perceptual grouping, spatial location, flicker fusion, visual search, global precedence, temporal order, and reading.

The kit also includes five neutral density filters with visible transmittances, preferably of 15%, 30%, 45%, 60% and 75%.

The test procedure is as follows. Firstly, the patient's preferred level of diffusion combined with chromatic selection and visible transmittance is established. This is achieved by selecting one of the filters and having the patient carry out a perceptual task which is transient-deficient-sensitive. These steps are repeated a number of times until the filter giving the best performance is ascertained. This then becomes the preferred filter.

Finally, the selected diffuser with chromatic selection filter is tested with a reading or reading related task. The patient's perfomance with the preferred filter is compared with his or her perfomance with a neutral density filter with the same level of visible transmittance. The final prescription is a light diffusing chromatic filter in the form of a pair of optical, frame mounted lens. Since each eye of the patient may be different, the prescription for each eye may well be different also.

The foregoing describes only some embodiments of the present invention and modifications, obvious to those skilled in the art, can be made thereto without departing from the scope of the present invention.

For example, it will be apparent to those skilled in the art that the present invention utilizes a new combination of optical techniques and equipment, each of which is known per se without combination. Accordingly, the invention once understood by those with optical skills is able to be easily implemented using techniques with which such skilled persons will be familiar.

What we claim is:

1. A test kit for testing an eye of a patient for impaired transient response, said kit comprising, in combination:
   means to enable an object illuminated with visible light to be viewed through a combination of a diffuser and a chromatic filter;
   a set of different combination diffusion and chromatic filters each of which, in differing degrees from filter to filter, removes an amount of high spatial frequency information above a corresponding predetermined number of cycles per degree from the light from said object, attenuates the levels of components of said light stimulative of red and/or green cones of the patients' eye relative to components of said light stimulative of the blue cones of the patients' eye, and attenuates the total amount of light transmitted through the filter; and
   a plurality of transient sensitive perceptive task objects and a plurality of reading related task objects.

2. A kit as claimed in claim 1 wherein the total visible transmittance of said filters varies between about 15% to about 75% and removal of said high frequency spatial information is effective from about 12 cycles per degree to about 25 cycles per degree, measured at substantially 100% contrast.

3. A kit as claimed in claim 2 having 25 combination diffusion and chromatic filters with transmittance values of 15%, 30%, 45%, 60% and 75% and effective high spatial information removal from 12, 14.4, 17.3, 20.7, and 24.9 cycles per degree respectively.

4. A kit as claimed in claim 3 further including five neutral density filters with visible transmittances of 15%, 30%, 45%, 60% and 75%.

5. A kit as claimed in claim 1 wherein said task objects are selected from the group of tasks consisting of perceptual grouping, spatial location, flicker fusion, visual search, global precedence, temporal order, and reading.

6. A method of reducing the impact of a reading deficiency caused by a slow transient response of a reader, said method comprising the steps of inserting a light diffusion means in the reader's light path to attenuate the high spatial frequency information mediated by the cone receptors of an eye of the reader, and inserting a chromatic filter which limits stimulation of the red and/or green cone receptors relative to stimulation of the blue cone receptors in the eye of the reader whereby the magnitude of the cone mediated sustained response of the reader's eye is reduced towards a more normal balance relative to the impaired transient response of the reader's eye.

7. A method of testing an eye of patient for impaired transient response comprising the steps of:
   1) selecting one combination diffusion and chromatic filter from a set of such filters each of which, in differing degrees from filter to filter, removes, from light passing through the filter, an amount of high spatial frequency information above a corresponding predetermined number of cycles per degree, attenuates the levels of stimulation by said light to red and/or green cones of the patient's eye relative to blue cones of the patient's eye, and attenuates the total amount of light transmitted therethrough;
   2) having the patient carry out a perceptive task sensitive to transient response by viewing a task object through said selected combination filter,
   3) carrying out steps (1) and (2) with other selected filters as necessary to determined an optimum combination filter, and
   4) having the patient carry out a reading related task by viewing a task object through the optimum combination filter.

8. A method as claimed in claim 7 wherein said optimum combination filter is used while the patient is tested using a reading related task, and the result compared with the patient's performance at substantially the same task utilizing a neutral density filter.

9. Apparatus for reducing the impact of a reading deficiency caused by a too slow transient response of a reader, said apparatus comprising light diffusion means and chromatic filter means for modifying light passing through said diffusion means and filter means to an eye of the reader for limiting the red and/or green mediated sustained response relative to the blue cone mediated transient response of the reader's eye, and location means to locate said diffusion means and filter means in the reader's light path.

10. Apparatus as claimed in claim 9 wherein said diffusion and filter means are combined within an optical lens.

11. Apparatus as claimed in claim 10 wherein the combined diffusion and filter means appears blueish in colour and attenuates spatial frequency information having a frequency higher than 10 cycles per degree.

12. Apparatus as claimed in claim 10 wherein said lens is selected from the group consisting of two spaced planes of glass or crystal, a wrinkle surface, a diffraction grating, and gradient index lenses.

13. Apparatus as claimed in claim 10 wherein said location means comprises a frame for spectacles.

* * * * *